United States Patent [19]

Blehaut et al.

[11] Patent Number: 5,665,352
[45] Date of Patent: Sep. 9, 1997

[54] PROCESS FOR REDUCING THE EXTENT OF CRYPTOSPORIDIUM DIARRHOEAS

[75] Inventors: Henri Blehaut, Neuilly sur Seine; Bernard Hublot, Compiegne, both of France

[73] Assignee: Laboratoires Biocodex, Montrouge, France

[21] Appl. No.: 321,908

[22] Filed: Oct. 12, 1994

[30] Foreign Application Priority Data

Oct. 25, 1993 [FR] France .................... 93 12692

[51] Int. Cl.$^6$ ................ A01N 63/04; A01N 63/00
[52] U.S. Cl. .................. 424/93.51; 435/255.2; 514/867
[58] Field of Search .............. 424/93.51; 435/255.2, 435/940; 514/867

[56] References Cited

U.S. PATENT DOCUMENTS 4,595,590  6/1986  Hublot et al. .................. 424/93.51

FOREIGN PATENT DOCUMENTS 0 149 579  7/1985  European Pat. Off. .
0 195 870  10/1986  European Pat. Off. .
3 501  8/1965  France .

*Primary Examiner*—Blaine Lankford
*Attorney, Agent, or Firm*—Young & Thompson

[57] ABSTRACT

Process for reducing the extent of *Cryptosporidium diarrhoeas*, which comprises administering to a patient in need thereof a therapeutically effective amount of yeasts of the *Saccharomyces boulardii* species. The yeasts are freeze-dried living yeasts. The yeasts are provided in the form of unit doses containing 0.050 to 3.0 g of yeasts.

3 Claims, No Drawings

PROCESS FOR REDUCING THE EXTENT OF CRYPTOSPORIDIUM DIARRHOEAS

The present invention relates to the use of yeast of the genus Saccharomyces for controlling cryptosporidiosis.

Cryptosporidiosis is a parasitic and contagious disease due to a protozoan Cryptosporidium. It affects numerous animals including man and the majority of domestic mammals (calves are often affected). It is observed worldwide, in adults and in children: in western countries 0.6 to 4.3% of children visiting a doctor for gastroenteritis are Cryptosporidium carriers. This rate varies from 3 to 30% in the Third World and rises to 63% during diarrhoea epidemics in children staying in nurseries (Plorde J. J. Cryptosporidiose. In Principles of Internal Medicine, HARRISON ed. 1991, 12th edition, McGraw-Hill).

The usual form of this disease is *Cryptosporidium diarrhoea* which manifests itself in man in two different forms depending on the breeding ground:

In immunocompetent subjects (especially children, travellers, hospital staff, veterinary doctors), the beginning is sudden with an acute, aqueous, abundant and explosive diarrhoea associated with abdominal cramps, the diarrhoea being cured spontaneously and completely within a few days to three weeks (12 days on average).

In immunosuppressed subjects (Aids patients for example), the beginning is more insidious and the diarrhoea more intense, going up to 17 liters per day. This diarrhoea persists, in this case, for life except if the immune deficiency is corrected.

The treatment of cryptosporidiosis is difficult and delusive. The efficacy of certain products is reported in an anecdotal and contradictory manner. In spite of several research routes, "the lack of effective treatment in immunosuppressed subjects remains certainly the major problem with cryptosporidiosis" (VERDON R., BELLHASAN D., RENE E. La Cryptosporidiose. Gastroenteral Clin. Biol. 19921 16:351–358). It would therefore be valuable to have an anti-Cryptosporidium agent, especially if it is not very harmful and is easy to use.

Moreover, it is known that yeasts of the genus Saccharomyces, such as *Saccharomyces boulardii* and *Saccharomyces cerevisiae*, have been used for a long time in the prevention and treatment of gastrointestinal tract disorders, in particular diarrhoea or colitis associated with the administration of antibiotics, with acute amoebiasis or with the after-effects of amoebiasis (see for example BE-A-652 331, EP-0-195 870 BA and FR-M-3501). These yeasts are generally administered orally, in the form of gelatin capsules containing 0.050 to 0.250 g of product, the daily doses usually being between 0.2 and 10.0 g for adults.

It has, however, never bean suggested that this type of yeast can allow the treatment of cryptosporidiosis.

Yet, it has now been found that living yeasts of the genus Saccharomyces substantially reduce the extent of *Cryptosporidium diarrhoeas* and can be used to treat cryptosporidioses.

Consequently, the present invention relates to a process for reducing the extent of *Cyrptosporidium diarrhoeas*, by administering to a patient in need thereof a therapeutically effective amount of yeasts of the *Saccharomyces boulardii* species.

Preferably, the yeasts used are yeasts kept alive by freeze-drying. They can be administered especially in a daily dose of 0.5 to 10 g (based on their weight in the freeze-dried form). More especially, the yeasts used according to the invention belong to the species *Saccharomyces boulardii*.

The yeasts can be administered orally, in unit doses ranging from 0.050 to 3.0 g, for example in the form of gelatin capsules containing about 0.250 g or sachets containing 0.050 to 3.0 g of yeasts.

But, of course, other forms of presentation, such as suspensions, and other routes of administration can be used.

A report of a clinical trial demonstrating the efficacy of Saccharomyces yeasts in the treatment of cryptosporidiosis will be given below.

A double blind study was carried out against a placebo under the following conditions:

1. Products: freeze-dried *Saccharomyces boulardii*. Origin: Biocodex Laboratories (France). The yeasts were packaged in sachets containing 500 mg of yeasts. The placebo was packaged in sachets containing a powder without pharmacological effect, as identical as possible in its appearance to the yeasts.
2. Treatment: The treatment consisted of 6 sachets of yeasts or placebo per day for 7 days.
3. Patients: 7 patients suffering from cryptosporidiosis associated with an acquired immunodeficiency syndrome were treated, 3 with yeasts (1 woman and 2 men) and 4 with the placebo (4 men). The diagnosis of cryptosporidiosis was related to the parasitological examination of stools and/or the anatomicopathological examination of stools and/or the anatomicopathological examination of the digestive mucosa.
4. Quantitative assessment of the state of the digestive transit: the latter was assessed by surveillance of a daily score of diarrhoea taking into account the number, the volume and the consistency of the stools (HART G., DOBB G. Effect of a faecal bulking agent on diarrhoea during enteral feeding in the critically ill. J Parent Ent Nut 1988; 12:465–468), and on the daily number of stools.
5. Results: the digestive transit was assessed before treatment and after one week of treatment. The results are summarized in the table below (median values):

|  | Yeasts | Placebo |
| --- | --- | --- |
| Number of patients | 3 | 4 |
| Diarrhoea score before treatment | 85 | 70.5 |
| Number of stools before treatment | 6 | 5.5 |
| Diarrhoea score after one week | 15 | 77.5 |
| Number of stools after one week | 2 | 6 |

No toxicity attributable to the product was observed.

In human, the freeze-dried *Saccharomyces boulardii* yeasts have an unquestionable effect on *Cryptosporidium diarrhoea*.

We claim:

1. Process for reducing the extent of *Cryptosporidium diarrhoeas*, which comprises administering to a patient in need thereof a therapeutically effective amount of living yeasts of the *Saccharomyces boulardii* species.

2. Process according to claim 1, in which the yeasts are freeze-dried living yeasts.

3. Process according to claim 1, in which the living yeasts are provided in the form of unit doses containing 0.050 to 3.0 g of living yeasts of the *Saccharomyces boulardii* species.

* * * * *